United States Patent [19]

Yaksh et al.

[11] Patent Number: 5,180,716
[45] Date of Patent: Jan. 19, 1993

[54] CYCLODEXTRIN COMPLEXES FOR NEURAXIAL ADMINISTRATION OF DRUGS

[75] Inventors: Tony L. Yaksh, San Diego, Calif.; Harlan F. Hill, Seattle, Wash.

[73] Assignee: The Regents of the University of California, Oakland, Calif.

[21] Appl. No.: 560,614

[22] Filed: Aug. 1, 1990

[51] Int. Cl.$^5$ .................... A61K 31/56; C08B 37/16
[52] U.S. Cl. ...................................... 514/58; 536/103
[58] Field of Search ......................... 536/103; 514/58

[56] References Cited

U.S. PATENT DOCUMENTS

| | | | |
|---|---|---|---|
| 4,599,327 | 7/1986 | Nogradi et al. | 514/58 |
| 4,603,123 | 7/1986 | Chiesi et al. | 514/58 |
| 4,727,064 | 2/1988 | Pitha | 514/58 |
| 4,816,462 | 3/1989 | Nowicky | 514/468 |
| 4,834,985 | 5/1989 | Elger et al. | 424/488 |
| 4,869,904 | 9/1989 | Uekama et al. | 514/58 |
| 4,983,586 | 1/1991 | Bodor | 514/58 |
| 4,983,636 | 1/1991 | Takeuchi et al. | 514/58 |
| 5,002,935 | 3/1991 | Bodor | 514/58 |
| 5,008,386 | 4/1991 | Szabo et al. | 536/103 |
| 5,017,566 | 5/1991 | Bodor | 514/58 |

FOREIGN PATENT DOCUMENTS 327766 8/1989 European Pat. Off.
3315356 11/1983 Fed. Rep. of Germany.

OTHER PUBLICATIONS

Anderson, W. R. et al., 1988. *Drug Design and Delivery* 2: 287-298.
Yaksh, T. L. et al., 1986. *Anesthesiology* 64: 54-66.
Koizumi, K. et al., 1981. *J. Chromatography* 205: 401-412.
Pitha et al., "Drug Solubilizers to Aid Pharmacologists: Amorphous Cyclodextrin Derivatives," *Life Sciences*, 43:493-502 (1988).
Pitha et al., "Hydroxypropyl-$\beta$-Cyclodextrin: Preparation and Characterization; Effects on Solubility of Drugs," *International Journal of Pharmaceutics*, 29:73-82 (1986).
Joseph Pitha, "Cyclodextrins: Solutions to Insolubility," *Neurotransmissions*, 5:1-4 (1989).
A. F. Casy et al., "Application of Cyclodextrins to Chiral Analysis by $^1$H N M R Spectroscopy," *Magn. Reson. Chem.*, 26:765-774 (1988).
Kawasaki et al., "Prostaglandin $E_2$ . $\beta$-Cyclodextrin (PGE$_2$ . CD) Pharmacological Studies on $\beta$-Cyclodextrin Clathrate Compound of Prostaglandin $E_2$ (PGE$_2$ . CD)," *Pharmacometrics* (Tokyo), 8:61-83 (1974).
C. Simone et al., "Beta -Cyclodextrin-Piroxicam: Efficacy and Tolerability in the Treatment of Pain After Bone and Joint Surgery," *Current Therapeutic Research*, 47:541-547 (1990).

*Primary Examiner*—Ronald W. Griffin
*Attorney, Agent, or Firm*—Christensen, O'Connor, Johnson & Kindness

[57] ABSTRACT

A method of delivering a drug to a patient, comprising administering said drug to the neuraxis of said patient in the form of a complex between said drug and a cyclodextrin, the cyclodextrin comprising at least one substituent to reduce crystallization of the complex or the cyclodextrin. Compositions suitable for carrying out the method are also disclosed.

21 Claims, 5 Drawing Sheets

CYCLODEXTRIN COMPLEXES FOR NEURAXIAL ADMINISTRATION OF DRUGS

TECHNICAL FIELD

This invention relates to compositions and methods for administering drugs to the neuraxis of a patient.

BACKGROUND OF THE INVENTION

From a therapeutic standpoint, a large number of drugs are employed for their central nervous system action. Examples of such classes of agents are centrally acting analgesics, antineoplastic agents, cerebral ischemia protectants, and compensatory therapeutic agents for central disorders such as Alzheimer's or schizophrenia. Other examples include drugs targeted to a variety of central nervous system disorders.

The spinal (intrathecal/epidural) administration of the centrally acting drugs described above has been shown to have considerable therapeutic efficacy for the treatment of several clinical states including pain, spasticity, central nervous system tumors and infections. In particular, the epidural administration of opioid analgesics represents an important clinical tool for the management of acute and chronic pain states Yaksh, T. L., Noueihed, R. Y., Durant, P. A. C.: *Anesthesiology* 64:54-66 (1986). The drug most commonly employed is morphine. Its kinetics are characterized by slow onset and a prolonged residency time in cerebrospinal fluid (CSF) Payne, R.: *Acta Anaestheiol. Scand.* (31, suppl.) 85:38-46 (1987). Sufentanil and other anilinopiperidines may be important alternatives to morphine by this route. These are powerful mu opioid receptor agonists that appear to have a higher intrinsic efficacy than morphine Stevens, C. W., Yaksh T. L.: *J. Pharmacol. Exp. There.* 250:1-8 (1989) and have higher lipid partition coefficients, indicating that these drugs will have a rapid onset.

Unfortunately, neuraxial administration of centrally acting drugs has some drawbacks. Most problematic is the fact that these drugs also achieve significant plasma concentrations after their administration. For example, epidurally administered drugs have several routes for redistribution: (a) movement into fat; (b) passage through the dura and thence into the spinal cord; and (c) most importantly, movement into the thin-walled epidural venous plexus and thence into the systemic circulation Yaksh, T. L.: Pain 11:293-346 (1981). Thus, following spinal administration of sufentanil or alfentanil, there are prominent blood concentrations of opioids early on which correspond with the rapid egress of drug from the epidural space Sabbe M. B., Yaksh T. L.: *J. Pain and Symp. Manag.* in press (1990). This vascular redistribution clearly results in powerful and acute supraspinal side effects. Such side effects are often serious and sometimes fatal.

A key goal of the present invention has been to develop improved methods that will allow the routine, acute and chronic administration of agents into the neuraxis via intraventricular, epidural, intrathecal, intrasisternal and related routes (hereafter jointly referred to as neuraxial routes) without the redistribution problem detailed above. An ideal therapeutic modality requires: (a) the prolonged and predictable presence of therapeutic concentrations of neuraxially-administered drugs at or near their sites of action in spinal cord or brain; (b) the limitation of drug distribution to the desired site of action within the CNS (i.e., minimization of its movement into the vasculature); and (c) the availability of a vehicle which permits the delivery of large concentrations of drugs in relatively small volumes. Typically, administration of drugs by the neuraxial routes may be limited by their relative solubility in water or lipids and/or factors that govern their kinetics and make them less than fully effective. Thus, agents with high lipid partition coefficients may require unusual vehicles that are not routinely biocompatible. Similarly, such lipophilic agents may be cleared very rapidly after neuraxial administration, giving them a short residence time in spinal or brain tissue and leading to unacceptably high peripheral plasma or tissue concentrations. These characteristics may lead to the failure of a particular drug or significantly limit its utility. The development of a vehicle that can alter the rate at which agents may undergo redistribution, render the agent soluble, maintain its bioavailability, and be compatible with the neuraxis of a patient would be of particular significance.

The inventors are the first to recognize that the problems associated with neuraxial administration of drugs may be ameliorated by administering a drug or drugs to the neuraxis of a patient in the form of a complex between the drug and a cyclodextrin. Cyclodextrin complexes with other types of drugs and/or for other routes of administration have previously been known. For example, U.S. Pat. No. 4,869,904 is directed to a sustained release drug preparation made up of an inclusion complex between a drug and a cyclodextrin derivative. Neuraxial administration of these prior complexes was not reported. In contrast to this prior work, the present applicants have discovered that complexes between cyclodextrins and drugs, when administered to the neuraxis of a patient, can, inter alia, reduce or retard diffusion or passage of the drug into the vasculature of a patient and, in some cases, increase the effectiveness of the drug in vivo.

Pitha, J., et al. *Life Sciences* 43:493-502 (1988), discusses the use of cyclodextrin derivatives to dissolve drugs. In one portion of this paper, it discloses intracerebral injection of a cyclodextrin derivative complexed with alkylating pindolol. In contrast to the present invention, alkylating pindolol is not a therapeutic drug, so its complex with the derivatized cyclodextrin is not a drug:cyclodextrin complex as used herein. More importantly, this prior reference does not disclose any advantages of administering a drug:cyclodextrin complex to the neuraxis of a patient.

Another prior publication of interest, Kawasaki, A. et al. Pharmacokinetics 8:61-63 (1974), discusses pharmacological studies on $\beta$-cyclodextrin clathrate compounds with prostagladin $E_2$. In this work, the prostaglandin molecule was administered to animals by a variety of routes, including oral, intravenous and intracisternal. However, these authors concluded that $\beta$-cyclodextrin showed no effect in their system. It is important to note that the cyclodextrins used to form drug complexes for the purposes herein must be derivatized relative to the parent cyclodextrin as will be discussed further herein. The cyclodextrin molecule used in this prior publication was unsubstituted.

Applicants are not aware of any prior reports of administration of complexes between drugs and substituted cyclodextrins to the neuraxis of a patient, as disclosed in greater detail herein below.

SUMMARY OF THE INVENTION

The present inventors have discovered that administration of complexes between drugs and substituted cyclodextrins to the neuraxis of a patient provides superior results as compared to administration of the drug alone. The cyclodextrins of the present invention have hydrophilic exteriors and relatively hydrophobic interiors and are capable of forming complexes with a variety of neuraxially-active drugs. Administration by this means represents an important way to prevent free clearance of the drug from the central nervous system or epidural space into the vasculature of the patient and may facilitate diffusion of the drug into the spinal cord or brain, thus increasing its availability at specific receptor sites in the central nervous system after administration.

DETAILED DESCRIPTION OF THE PREFERRED EMBODIMENTS

Figure 1A:
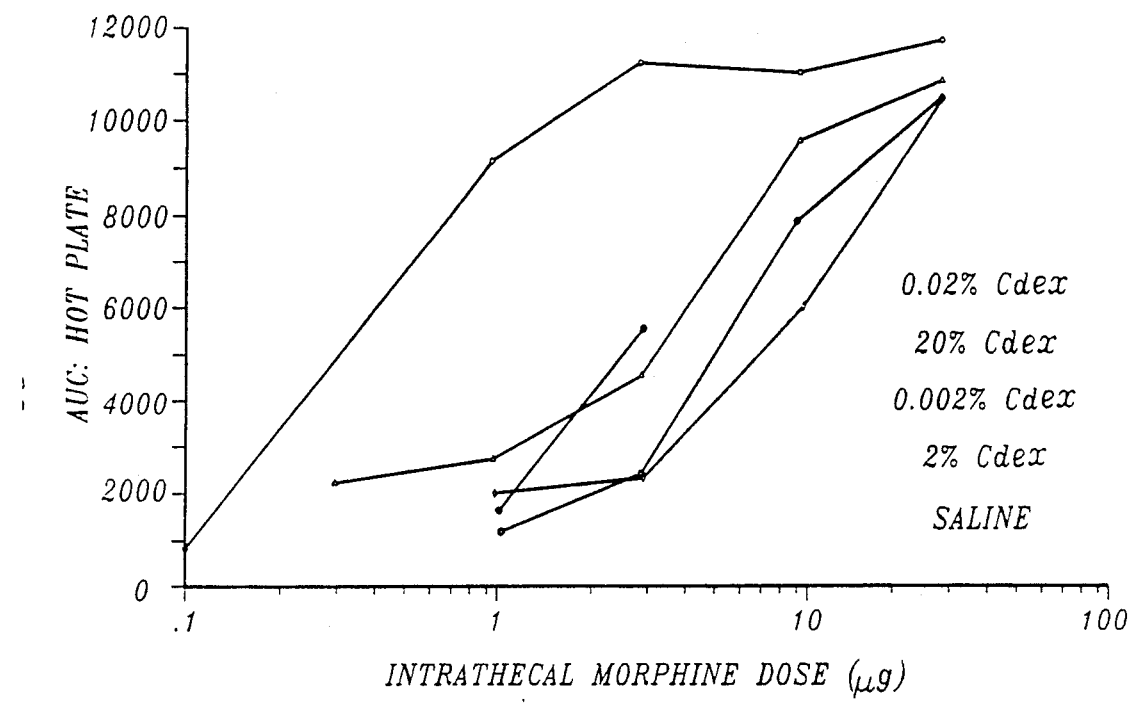
FIGS. 1A and 1B show the area under the time effect curve (AUC) measured on the hot plate (52.5° C.) versus the intrathecal dose of lofentanil (FIG. 1B) and morphine (FIG. 1A) administered in saline or in the presence of several concentrations of a cyclodextrin. Each point presents the mean of four to eight animals. Note that the Y-axis of the lofentanil and morphine curves are different. Standard error indicators are deleted for clarity. By one way ANOVA and subsequent Newman Keuls statistical tests, the effects observed at the highest dose of of lofentanil are ordered ($p<0.05$): 2%, 0.02%, 20%, 0.002%, saline; for morphine, the ordering at the 10 microgram dose is: 0.02%, 20%, 0.002%, 2%, saline.

In accordance with the present invention, it has now been recognized that many of the problems associated with neuraxial administration of drugs to patients can be solved or minimized by administering the drugs in the form of complexes with cyclodextrins. For the purposes of the present invention, unsubstituted cyclodextrins, that is, those that have not been modified with substituents, are not desirable, at least in part because it is more likely that they will crystallize or otherwise precipitate out of solution in vivo.

Generally speaking, cyclodextrins are cyclic compounds having a cylindrical molecular structure wherein the inner surface and the outer surface are different in their hydrophilic or lipophilic nature, thus permitting other molecules, known as "guest molecules," of suitable dimensions, or parts thereof, to penetrate into the intramolecular cavity of the inner part of the cylindrical cyclodextrin "host molecule," thereby forming an inclusion complex. In some instances, the drug may form a complex with the cyclodextrin at a site different from the intramolecular cavity of the cyclodextrin. Both types of complexes are contemplated to form part of the present invention. For the majority of drug: cyclodextrin combinations, the inclusion complex will be the predominant or sole complex formed; thus, inclusion complexes are generally preferred for the purposes disclosed herein.

To be useful in connection with the present invention, a cyclodextrin molecule must be capable of forming a complex with a drug of interest and both the cyclodextrin and the inclusion complex must be compatible with neuraxial administration. In structural terms, the cyclodextrin that may be used in connection with the present invention will be composed of saccharide moieties linked so as to form a cylindrical structure, having an intramolecular binding cavity. The saccharide moieties may be any of those that can be coupled together either directly or through molecular linkers to form structures that are capable of binding to a drug for neuraxial administration. The well-known "natural" cyclodextrins are composed of D-glucopyranose bound together by 1,4 linkages. Any of these compounds are useful for the purposes of the present invention, when derivatized as discussed further below. Typically, these preferred compounds will be made up of six, seven or eight molecules of D-glucopyranose. These cyclodextrins are referred to in the art as alpha, beta, and gamma cyclodextrins, respectively.

It is well known that some types of cyclodextrins are capable of crystallizing in vivo, thereby interfering with normal processes, and may lead to renal damage or failure. See, for example, Pitha, J. et al. *Life Sciences,* 43:493-502 (1988); Pitha, J., et al. *International Journal of Pharmaceutics,* 29:73-82 (1986); and Pitha, J. *Neurotransmissions,* 5:1-4 (1989), each of which is hereby incorporated by reference. Cyclodextrin molecules that readily crystallize or precipitate from solution in vivo are not useful for the present purposes. To prevent this problem, the cyclodextrins of the present invention must be derivatized as compared to the parent cyclodextrin molecules. Thus, for example, with respect to alpha, beta, and gamma cyclodextrins, these parent molecules must be modified with substituents in a manner that interferes with or prevents their crystallization or precipitation from solution, especially under in vivo conditions.

The degree and manner of derivatization of the cyclodextrin is not specifically limited except that it must be sufficient to minimize the problems set forth above. The substituents are preferably hydrophilic so as to render the cyclodextrin more water soluble. Additionally, the cyclodextrin is preferably nonsymmetrically and incompletely substituted, which reduces its crystallizability. The substituents in accordance with the present invention are preferably selected from —$OCH_3$, —ROH, —R(OH)$_2$, —RSO$_3$H, —CO$_2$R, —NHR, —NR$_2$, —NROH, and —SiR$_3$, wherein each R is independently selected from C$_{1-10}$ alkyl groups that may be linear, branched, or cyclic. Particularly preferred substituents are —OCH$_3$ and —ROH. Where possible, pharmaceutically acceptable salts of the above groups are also encompassed by the present invention.

Each of the saccharide rings in the cyclodextrin may be substituted at the 2, 3, and 6 positions on the ring. In accordance with the present invention, any one of these sites or a combination of sites (e.g., 2 and 3, 2 and 6, 3 and 6, or 2 and 3 and 6) may be substituted with one or more of the substituents described herein. For example, in a preferred embodiment, the cyclodextrin molecule will be substituted asymmetrically with β-hydroxypropyl groups at some but not all the 2 positions. The most preferred cyclodextrin is β-cyclodextrin (having 7 glucose moieties) substituted (i.e., derivatized) with hydroxypropyl groups. A particularly preferred cyclodextrin is 2-hydroxypropyl-β-cyclodextrin (also referred to herein as CDEX).

Additional specific examples of substituents that may be attached to the saccharide molecules of the cyclodextrins are: hydroxyethyl, hydroxybutyl, hydroxypentyl, hydroxyhexyl, butylsulfonate, propylacetate, ethylamine, ethylene glycol, and the like.

In addition to pure substituted cyclodextrins, it is also possible in accordance with the present invention to utilize mixtures of cyclodextrins. In one specific example of such a mixture, a parent cyclodextrin (e.g., β-cyclodextrin) is derivatized asymmetrically to less than 100% so that the final composition contains both the parent cyclodextrin and a mixture of cyclodextrins substituted to differing degrees by hydroxypropyl groups. In this situation, it is useful to refer to an average degree of substitution of the overall mixture of cyclodextrins and to define the parent cyclodextrin as being zero percent substituted and the composition in which each cyclodextrin molecule is substituted at all molecular positions as being 100% substituted. For the purposes herein, the preferred degree of substitution ranges from 10% to 100%, with the more preferred range being from 15% to 80%. Lower or higher degrees of substitution may be required for particular drugs or for particular types of desired effects in vivo.

It is preferred, although not believed to be essential in all cases, that the drug be able to dissociate from the cyclodextrin complex in vivo so that the free drug is available for its intended pharmacological activity. Theoretical considerations suggest that the rate of dissociation is proportional to several variables, including: (a) the stability constant of the drug-cyclodextrin complex; (b) the relative amounts (e.g., molar ratio) of drug and cyclodextrin; and (c) the local concentration of cyclodextrin in the volume into which the complex is delivered. If there is a molar excess of cyclodextrin, the likelihood of finding free drug in solution or in the neuraxial space is proportionately diminished. In the case of the traditional routes of administration (e.g., intravenous or oral), the total volume of drug or the microencapsulated complex administered is diluted in a large, essentially infinite space or volume. Thus, the quantity of cyclodextrin employed may not be critical as long as it is sufficient to bind a significant proportion of the available drug and the rate of dissolution of the inclusion complex will be largely dependent on the stability of the complex. On the other hand, if the cyclodextrin drug complex is administered into a space or volume from which the drug, but not the cyclodextrin, may readily diffuse, then molar excesses of cyclodextrin will reduce proportionately the rate at which the drug molecule will be free to diffuse, i.e., free molecules will be in equilibrium with the excess binding sites provided by cyclodextrin. Based on this consideration, agents such as cyclodextrin injected into the epidural, intrathecal, or intraventricular spaces (as cyclodextrin-drug complexes) can have optimal concentrations or molar ratios of cyclodextrin to drug delivery, depending upon the rate at which the appearance of free drug is desired.

The freedom with which a complexed drug may exit the environment of the cyclodextrin cavity is a function of the size of the drug molecule, its shape, and its lipid solubility. Lipophilic drug molecules bind with greater affinity to the hydrophobic interior of the cyclodextrin. If the lipid solubility of the drug is too high, the drug may not dissociate at all, even when the complex approaches a lipid membrane; thus, some drugs would be rendered inactive since they would not reach specific receptors in tissue in an active form. In its simplest form, the interaction between a drug and a cyclodextrin resembles that of a competitive ligand, and as such obeys the law of mass action with affinity proportional to the lipid solubility and other physicochemical properties of the drug. Pitha, J.: Neurotransmissions Research Biochemicals, Inc., Massachusetts 5 (1989).

It is notable that increasing the degree of substitution on the cyclodextrin will increase the apparent binding affinity of lipophilic drugs for the cyclodextrin molecule. For opiods with high lipid solubility, it is expected that increased substitution will favor controlled release. However, for opioids with low to intermediate lipid solubility, a lower degree of substitution may be more favorable.

For purposes of the present invention, it is a relatively straightforward matter to determine whether a given cyclodextrin and drug combination is likely to be in vivo dissociable. It is well known that one may measure the affinity constant between a drug and a ligand by way of standard techniques. For example, the interaction between a cyclodextrin and a drug can be studied by equilibrium dialysis, or other suitable techniques. The equilibrium binding data can be analyzed by a standard Scatchard plot, which readily allows one to calculate the intrinsic ligand dissociation constant. Once a dissociation constant is known for a particular drug/cyclodextrin combination, a reasonable estimate can be made as to whether the complex will be dissociable in vivo. If the measured dissociation constant is higher than, for example, $10^{-6}$M in vivo dissociation may be expected not occur to any significant degree or to occur at very slow rate. The conditions under which the binding constant are measured may be rendered more similar to in vivo conditions by adjustment, for example, of pH and the concentrations of various ions, etc. Binding constants measured under these conditions may more closely approximate the binding constant under in vivo conditions.

It should be stressed that a slow rate of dissociation does not in theory exclude the utility of the cyclodextrin-drug complex. First, the dissociation is based on the law of mass action and if the drug is diffusing into a large volume, such as the CSF or the spinal cord, then the equilibrium conditions will permit the development of sustained steady state concentrations. Thus, the ability to define the dissociation constant can be used to predict a priori whether the drug complex will reach a high or low steady state concentration relative to the amount of drug administered. It would be possible, therefore, with this information to tailor the drug delivery profile. Agents with slow rates of dissociation would be given in larger amounts to achieve the given level of free drug in the appropriate biospace.

A second theoretical consideration mentioned above involves the relative concentrations of drug and cyclodextrin when given into a kinetically limited space. If the drug cyclodextrin-ratio is low and there is a large amount of cyclodextrin, then the concentration of free drug will be correspondingly diminished. In other words, the presence of excesses of unbound cyclodextrin will represent a reservoir of binding sites which will compete with the tissue for drug redistribution. It should be noted that this is fundamentally different from a systemic route of administration where the total cyclodextrin (bound and free) is distributed into an essentially infinite volume (the body vasculature tree) in contrast to the limited volume of the cerebrospinal fluid or epidural space. If too much cyclodextrin is administered with the drug, the drug activity will be diminished; if too little, then the redistribution of the drug into the vasculature will not be sufficiently delayed. Thus, there are three factors that particularly govern the neuraxial redistribution of the drug-cyclodextrin complex: the dissociation constant of the drug cyclodextrin complex, the drug/cyclodextrin ratio, and the total dose of cyclodextrin administered into the particular space. It can be seen that these variables will result in an optimal drug dose/cyclodextrin ratio and an important consideration is the ability to define these ratios with in vitro/in vivo models.

It is also contemplated in connection with this invention that some drug:cyclodextrin complexes will be pharmacologically active even though the drug has not dissociated from the complex. This could occur, for example, if the active portion of the drug were available for interaction at the target site (e.g., a specific receptor) even while the drug molecule was complexed by the cyclodextrin. Another possibility is that the drug could form a complex with a site on the cyclodextrin molecule other than the intramolecular cavity, i.e., on the surface of the cyclodextrin (i.e., drug binding to substituent groups, such as hydroxypropyl side chains). Such complexes also form part of the present invention.

In general, the molar ratio of drug to cyclodextrin can vary over a relatively wide range. The precise range will depend upon the mode of administration and the particular drug and cyclodextrins employed. For epidural administration, the molar ratio will generally range from about 1:10 to 1:10,000; for intrathecal and intraventricular administration, the molar ratio will generally range from about 1:10 to about 1:1,000. These ranges are given to exemplify typical ranges; they will not necessarily apply to every drug:cyclodextrin complex with useful neuraxial activity.

In order to ascertain whether a given inclusion complex has in vivo activity, standard tests in vivo models, such as those exemplified below, may be employed. Such tests will also readily provide information on whether there is a shift in the activity/time curve for a given complex. In vitro determination of binding constants between the drug and the cyclodextrin and ex vivo measurements of meningeal flux coupled with results in in vivo models therefore enable one to determine whether a given complex is active in vivo.

In the development of the use of cyclodextrins as a neuraxial delivery system, the inventors have employed several in vivo models in which the animal is chronically prepared with spinal intrathecal and/or spinal epidural catheters which allow nontraumatic injection of different drug agents in different vehicles. Using these models, the inventors were able to quantitatively define the effects and distribution characteristics of agents given by the several routes and to concurrently assess potential local toxicity and drug redistribution kinetics. Pharmacologically and toxicologically, these systems are highly predictive of effects in human patients.

In some of these preliminary studies, the inventors have observed that there were modest increases in the antinociceptive effects for morphine, but a highly significant increase in the duration of action for lofentanil after intrathecal administration in a cyclodextrin, as compared to a saline vehicle. No evidence of toxicity was observed in these preliminary studies.

In addition to the in vivo studies showing safety, efficacy, and further characterizing the role of the composition of the drug:cyclodextrin combinations on kinetics and drug activity, the inventors have also examined the influence of cyclodextrins on the rates of diffusion of particular model drugs, the opioid alkaloids, through live (ex vivo) samples of spinal cord dura matter, arachnoid matter and pia matter. These studies, reported in the examples below, can determine the extent to which various concentrations of cyclodextrin can regulate and thereby prolong the duration of, for example, spinal action of epidurally or intrathecally administered complexes of cyclodextrin. Thus, these models serve as ex vivo systems that permit the rapid approximation of the optimal cyclodextrin:drug ratio required for the use of the complexation procedure for other spinally administered agents, such as other opioids, and antineoplastic agents such as methotrexate and busulfan. Different components of the ex vivo meningeal permeability model are useful for predicting rates of diffusion of cyclodextrin complexes from the epidural space to the spinal cord (using the total meningeal complex to measure flux). This ex vivo research allows one to make useful predictions as to what concentration of the cyclodextrin (and ratios of cyclodextrin to drug) will provide optimal drug:cyclodextrin combinations for yielding prolonged residency time after intrathecal-/epidural administration.

The drugs that are useful for purposes of the present invention are not specifically limited, other than that they must be capable of forming a complex with a cyclodextrin and they must be suitable for administration to the neuraxis of a patient. By "neuraxis," as used herein, is meant any surface, region or volume of tissues that comprise the spinal cord, brain, or central nervous system. This would include, for example, the brain within the cranial cavity (intraventricular), the spinal canal (epidural), and the space between the dura-arachnoid mater and the pia mater (intrathecal). From a therapeutic standpoint, a large number of drugs are employed for such action. Typical of such classes of agents are centrally acting analgesics, antineoplastic agents, cerebral ischemia protectants, compensatory therapeutic agents for central disorders such as Alzheimer's or schizophrenia, and other drugs targeted to a variety of central nervous system disorders. Cancer chemotherapeutic agents such as methotrexate and busulfan are often employed in cases of central nervous system tumor involvement. Methotrexate is commonly used intrathecally to obtain high neuraxial concentration. Occasionally, neuraxial agents are employed to reduce the likelihood of cerebrospinal fluid seeding as in meningeal carcinomatosis. See Kooistra, K.L. et al., Cancer 46:317-323 (1986). Combinations of methotrexate and a cyclodextrin could alter favorably the redistribution kinetics after intrathecal or neuraxial administration. Busulfan, a highly lipophilic agent, is useful for neuraxial tumor reduction, but when administered orally, it causes severe bone marrow depression, similar to several other cancer chemotherapeutic agents. Combinations of busulfan with cyclodextrin may allow its effective neuraxial use. Similar advantages may be achieved for a variety of drugs used for nonmetastatic syndromes in which neuraxial concentrations of drug have been proven effective. Examples of these cases include neuraxial fungal and meningeal infections. Delivery of local anesthetics could also be carried out in this manner. Other conditions that may be treated are: spasticity, seizure disorders, and arachnoiditis.

It is probable that in the near future, therapeutic agents for AIDS and other virally mediated conditions may be approached in this manner by drugs which have unfavorable or poor pharmacokinetic properties. Agents such as cyclodextrin could be of considerable advantage in these instances, not just because they provide very useful, nontoxic solubilizing means, but because of their effects on drug bioavailability.

Other drugs that have formed the basis for several preliminary tests conducted by the inventors are the opioid analgesics suitable for central administration. Examples of such drugs are the following: alfentanil, sufentanil, lofentanil, fentanyl, and morphine.

The complexing methods according to this invention may be carried out by any of a number of standard methods known to those of ordinary skill in this art. The precise physical method of forming the complex is relatively unimportant for the present invention as long as the complex is formed by the time that it is present in the neuraxis of the patient. Specific methods that may be used are: the kneading method, solution method, lyophilizing method, or the like.

A preferred method of producing the complexes for administration to a patient involves providing an aqueous solution that contains an appropriate amount of a drug to be complexed and a cyclodextrin and allowing the well-mixed solution to stand for a suitable period of time (e.g., from about ½ hour to about 24 hours or more) to thereby allow a complex to form. The aqueous solution that is utilized to form the complex will generally be the same solution that is used to administer the complex. The drug:cyclodextrin complexes will preferably be administered to a patient in a physiologically acceptable medium, such as physiological saline containing standard additives for neuraxial administration of drugs. Preferred media are: dextrose (e.g., 1-5%) in sterile water or sterile water alone.

Confirmation of the formation of a complex of the drug with the cyclodextrin derivative may be confirmed by a variety of methods, including powder X-ray diffraction, dissolution behavior, scanning electron microscope analysis, differential thermal analysis, and infrared absorption.

The drug:cyclodextrin complexes described above may be administered to patients by standard procedures normally employed for administration of the uncomplexed drugs. The goal of such administration is to provide an effective amount of active drug to the neuraxis of a patient. As a first approximation, it is generally suitable to employ the standard dosages of the uncomplexed drugs to evaluate results with a given drug:cyclodextrin complex. However, in some instances, the activity of the drug will be enhanced (e.g., increased potency, increased efficacy, and/or increased duration) by administration as a complex with a cyclodextrin due, for example, to greater residence time of the active drug in its primary location of action and less supraspinal vascular or bulk flow redistribution. As a result, smaller doses of the complexed drug as compared to the uncomplexed drug may be found to be suitable for administration to a patient. The optimal dosage range may be determined by using standard animal models and/or actual clinical testing.

In general, the amount of the complex to be administered should be sufficient to effectively treat the condition being treated by a physician. Such conditions can include pain caused by a variety of disease states and/or injury, including cancer, pain caused by other stimuli (e.g., labor pain, post-surgical pain), spasticity, CNS tumors and infections, and a variety of other disease states targeted by the drugs summarized above. One of ordinary skill will be able to determine appropriate effective amounts using the standard models disclosed herein and/or standard pharmacologic testing techniques.

Exemplary modes of administration of the above-described drugs include epidural (administration into the peridural space); intrathecal (administration into the cerebrospinal fluid-containing space); intracranial (administration into the brain parenchyma); or intraventricular (administration into the cerebral ventricles).

Human patients are preferred; however, animal patients are also possible. Thus, veterinary uses are also contemplated for purposes of the present invention.

In addition to methods of administration of drugs, the present invention also covers compositions suitable for such administration, which comprise a drug complexed by a substituted cyclodextrin and standard media for neuraxial administration of a given drug. This could include standard surfactants or other drugs that do not form complexes but that interact physiologically or pharmacologically with the complexed drug (e.g., cyclodextrin: opioid with an $\alpha_2$-agonist such as dexmedetomidine).

The following examples are presented to illustrate the advantages of the present invention and to assist one of ordinary skill in making and using the same. These examples are not intended in ay way to otherwise limit the scope of the disclosure or the protection granted by Letters Patent hereon.

EXAMPLES

1. Drug Preparation

The 2 hydroxypropyl-$\beta$-cyclodextrin (CDEX: 40% substituted) was purchased from Research Biochemical Inc., Natick, MA. Other agents were obtained from the following sources: morphine sulfate (Merck); sufentanil citrate; alfentanil, HCl; and lofentanil oxalate (Janssen Pharmaceutica, also known as Janssen Research Foundation).

All drugs were prepared when indicated either in sterile saline or in cyclodextrin dissolved in distilled water at the indicated percentage. In these conditions, the weighed drug was dissolved by simple mixing and agitation. Capsaicin was also administered dissolved in dimethylsulfoxide (DMSO: reagent grade, Sigma Chemical) and then brought to final volume in saline. In the meningeal permeability studies, drugs with or without cyclodextrin were dissolved in artificial cerebrospinal fluid.

2. Toxicity Studies a. Lumbar intrathecal injections—rats: Rats (250–350 gm) were prepared with chronic intrathecal catheters placed in the lumbar intrathecal space. They received intrathecal administration of 15 μl of of 25% CDEX. There was no change either acutely or after 7 days in the motor function of these animals as assessed by the placing/stepping reflexes or bladder function (absence of urine stains on the abdomen). At 7 days, the levels of neuropeptides substance P and calcitonin gene-related peptide (CGRP) were measured after extraction of tissue, using radioimmunoassays. Tissue concentrations of these peptides, found in unmyelinated sensory afferent neurons, were unchanged when CDEX was administered in the absence of other agents. In contrast, the use of the vehicle dimethyl sulfoxide (25% in saline) resulted in a significant reduction in the levels of the two peptides.

b. Lumbar intrathecal injections—guinea pigs: Guinea pigs (male: 300–400 gm; N=12) were administered 20% CDEX by percutaneous puncture of the lumbar intrathecal space with a 30 gauge needle. There were no acute behavioral signs of agitation, indicating no irritation. There were no changes in the motor function of the animals as measured by placing, stepping and righting reflexes or ambulatory tests. No evidence of urine staining was noted.

c. Lumbar epidural injections—dogs: Beagle dogs (11–15 kg) prepared with lumbar epidural catheters received injections of 20% CDEX (2 ml; a standard volume of injection in this model). This treatment had no effect on the heart rate, bladder function or skin twitch response for periods of up to 7 days after each acute injection. These data indicate the lack of toxicity of spinal CDEX.

d. Intraventricular injections—rats: In rats prepared with chronic intracerebral ventricular (ICVT) cannulae and electroencephalographic electrodes, the ICVT injection of CDEX (20%; in a standard volume of 10 μl) had no effect upon general motor behavior, or EEG activity for periods of up to 7 days after injection.

3. Antinociceptive Activity a. Intrathecal injection—rats: effects of a fixed CDEX concentration on drug action. Rats prepared with lumbar intrathecal catheters received injection of different amounts of morphine, sufentanil, alfentanil or lofentanil. Injections were made in volumes of 10 μl of saline vehicle or in vehicle of 20% CDEX. For all drugs, there was a rightward shift in the intrathecal dose response curve (indicating increased potency) and an increase in the duration of antinociceptive effect. As shown in Table 1, the ordering of the magnitude of increase in the potency (i.e., decrease in $ED_{50}$) at this concentration of CDEX was: alfentanil; lofentanil; morphine; and sufentanil. Also indicated is that with the addition of CDEX, there was a significant increase in the area under the analgesia time course curve (indicating increased duration of action) for each of these four drugs.

TABLE 1

Effect of intrathecal 2-hydroxypropyl-β-cyclodextrin (20%) on the peak (MPE) and duration (AUC) of the antinociceptive effects in the rat of opioids given intrathecally on the hot plate test.

| Spinal Drug | $ED_{50}$ (μ) (1) Saline | $ED_{50}$ (μ) (1) CDEX | AUC-3000 (μg) (2) Saline | AUC-3000 (μg) (2) CDEX |
|---|---|---|---|---|
| Morphine | 4.0 | 1.1 | 1.7 | 0.5 |
| Alfentanil | 8.2 | 1.0 | 80. | 17. |
| Sufentanil | 0.2 | 0.06 | 0.5 | 0.2 |
| Lofentanil | 0.1 | 0.02 | 0.04 | 0.015 |

Figure 1B:
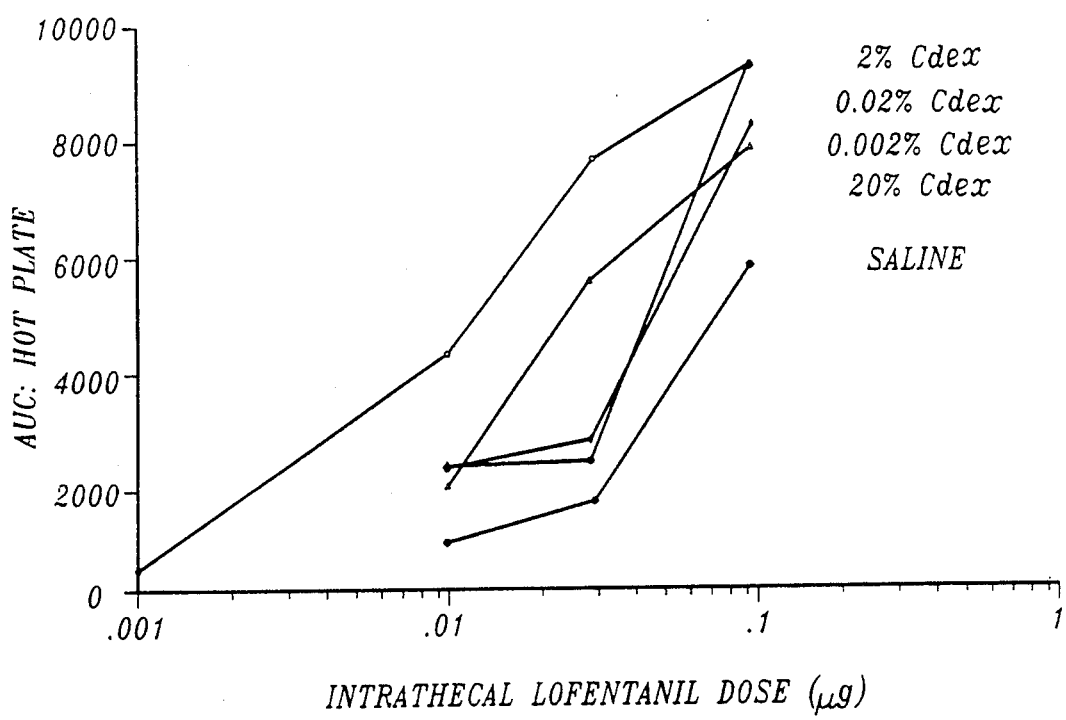
Figure 2A:
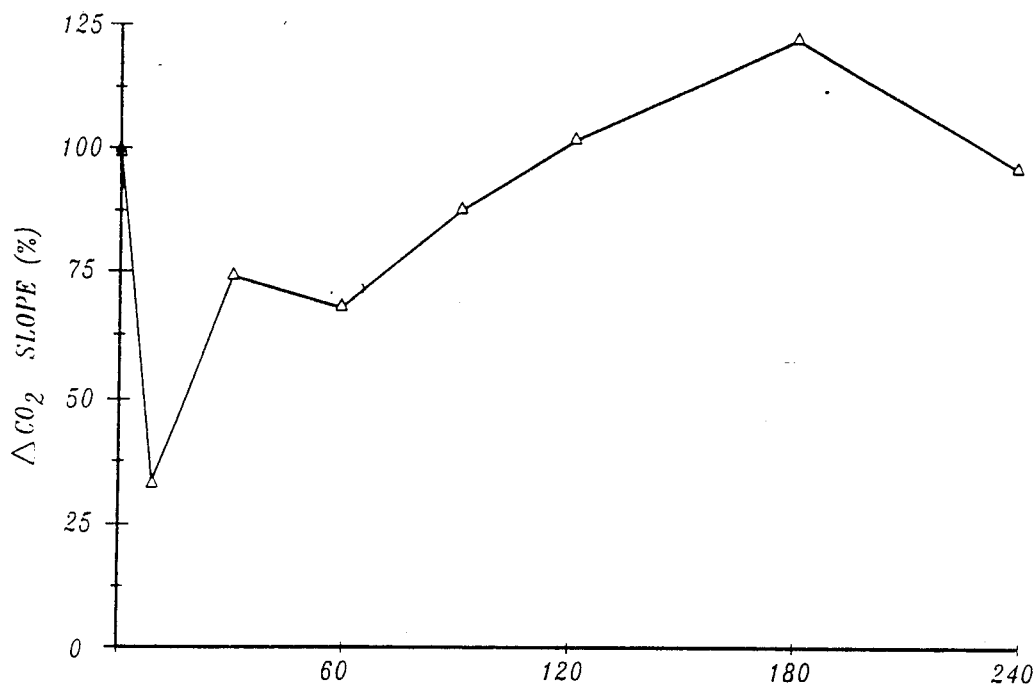
FIGS. 2A, 2B, 2C, 2D, 2E and 2F show the respiratory depressant effects of epidural treatments as percent decrease in the minute ventilation $CO_2$ function (FIGS. 2A and 2B); percent change in the threshold for thermal pain (FIGS. 2C and 2D) and the lumbar and cisternal cerebrospinal fluid (CSF) concentrations of drug (FIGS. 2E and 2F) in a dog in which the first injection was of alfentanil (400 micrograms) in saline (FIGS. 2A, 2C and 2E) and the second injection (given seven days later) was of alfentanil (400 micrograms) in 20% cyclodextrin (FIGS. 2B, 2D and 2F).
Figure 2B:
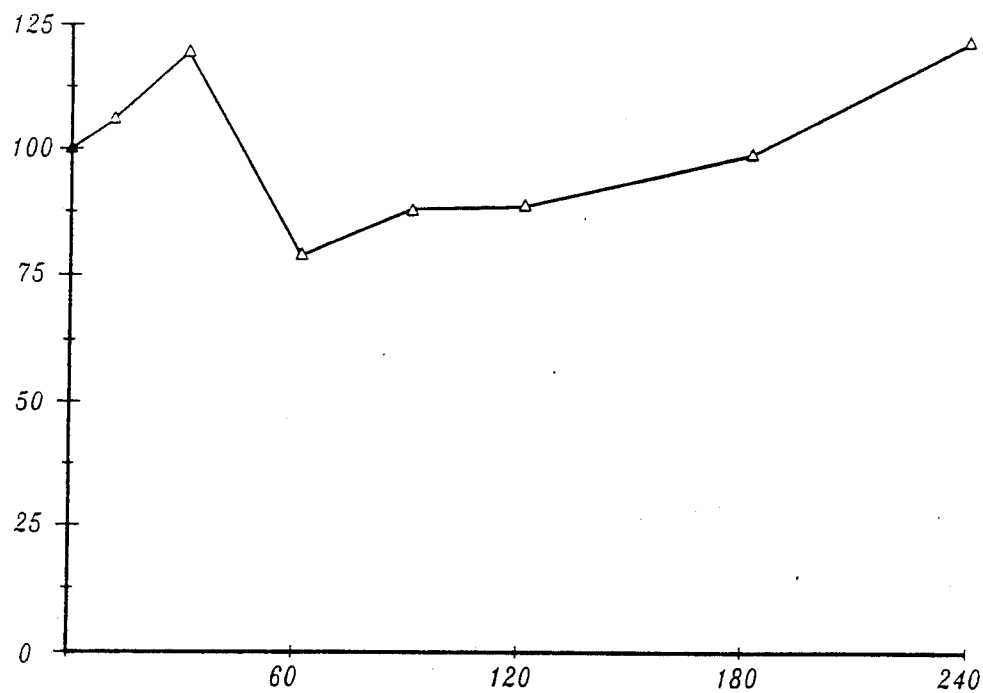
Figure 2C:
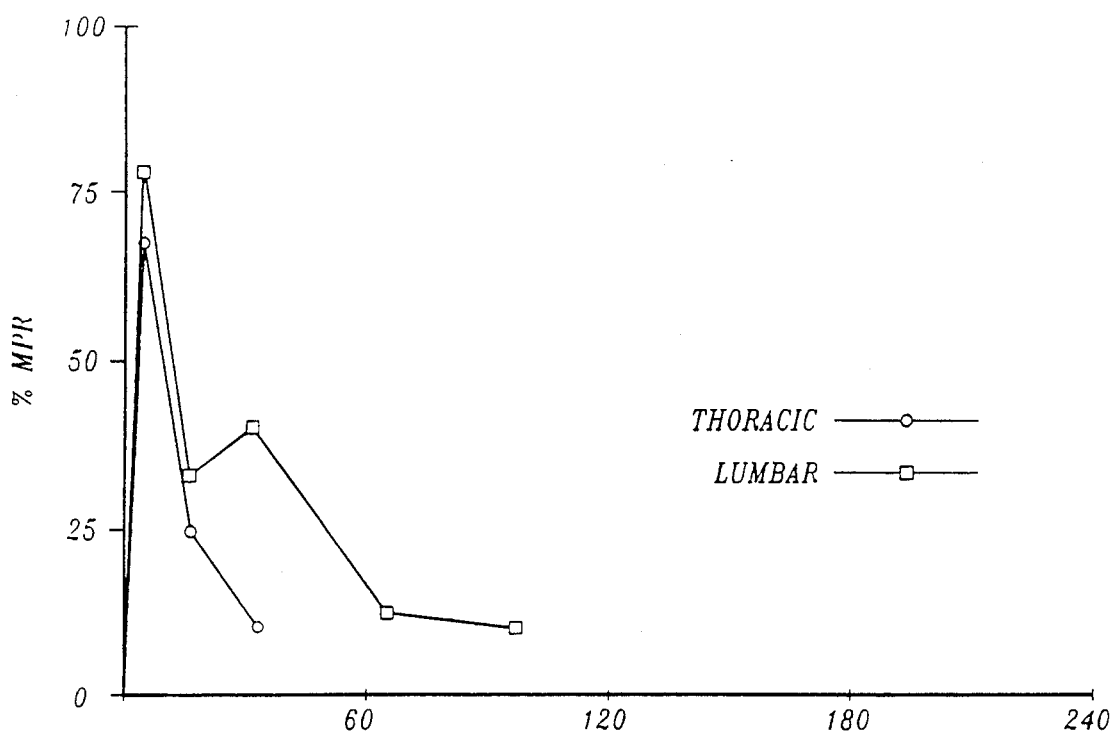
Figure 2D:
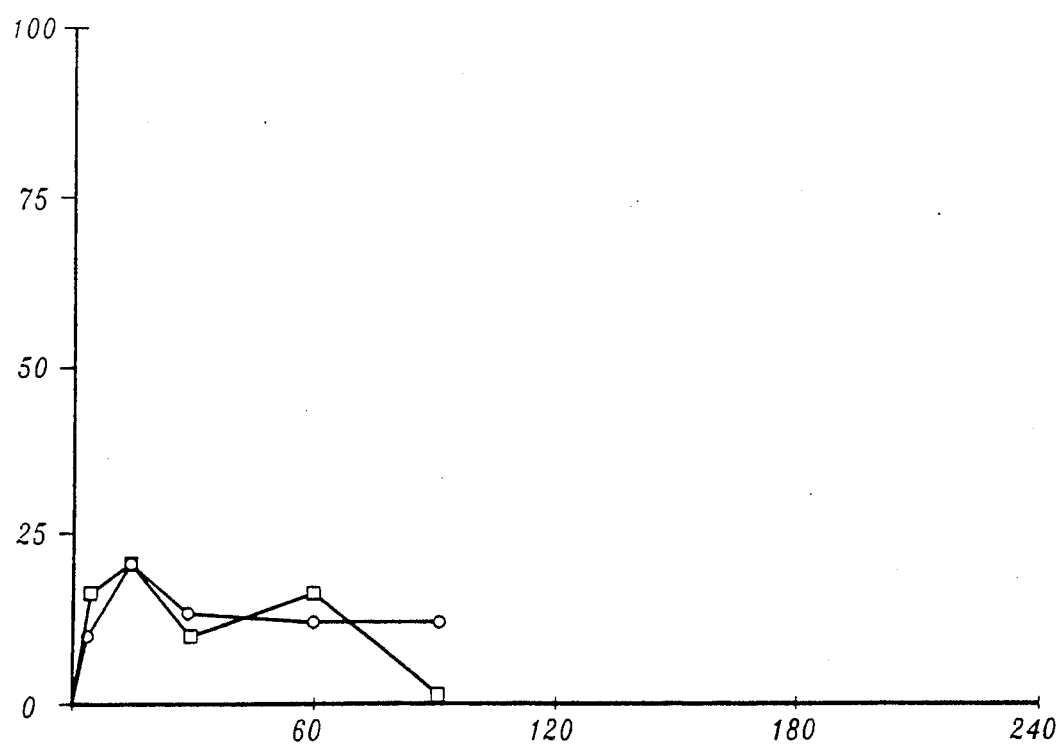
Figure 2E:
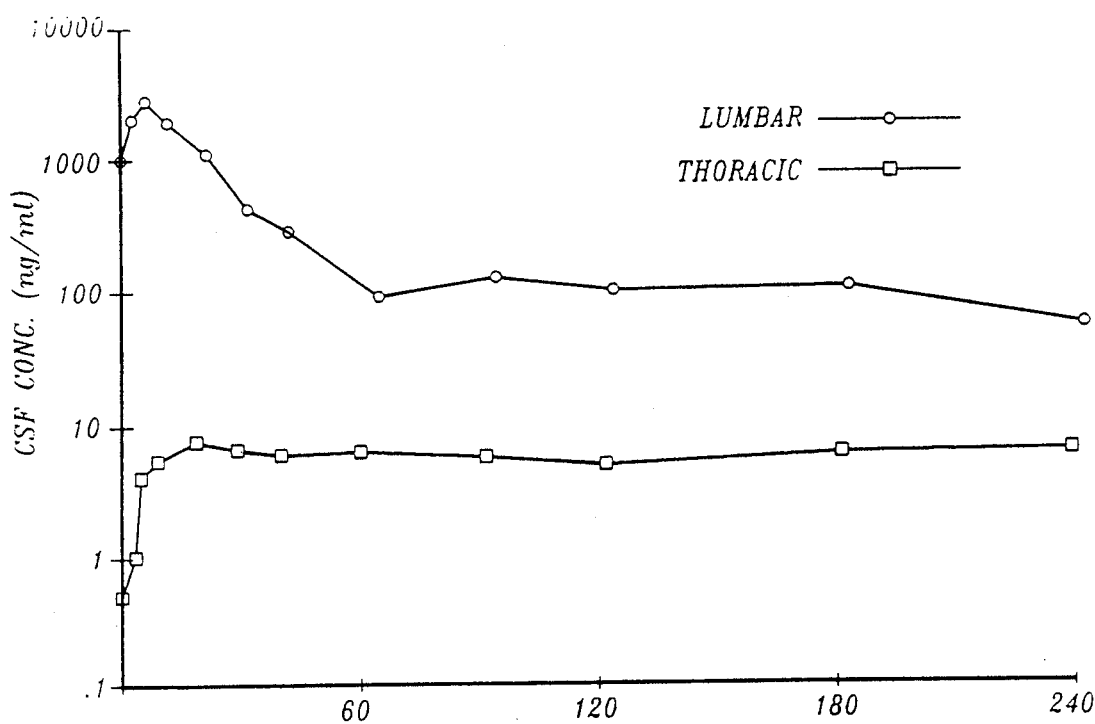
Figure 2F:
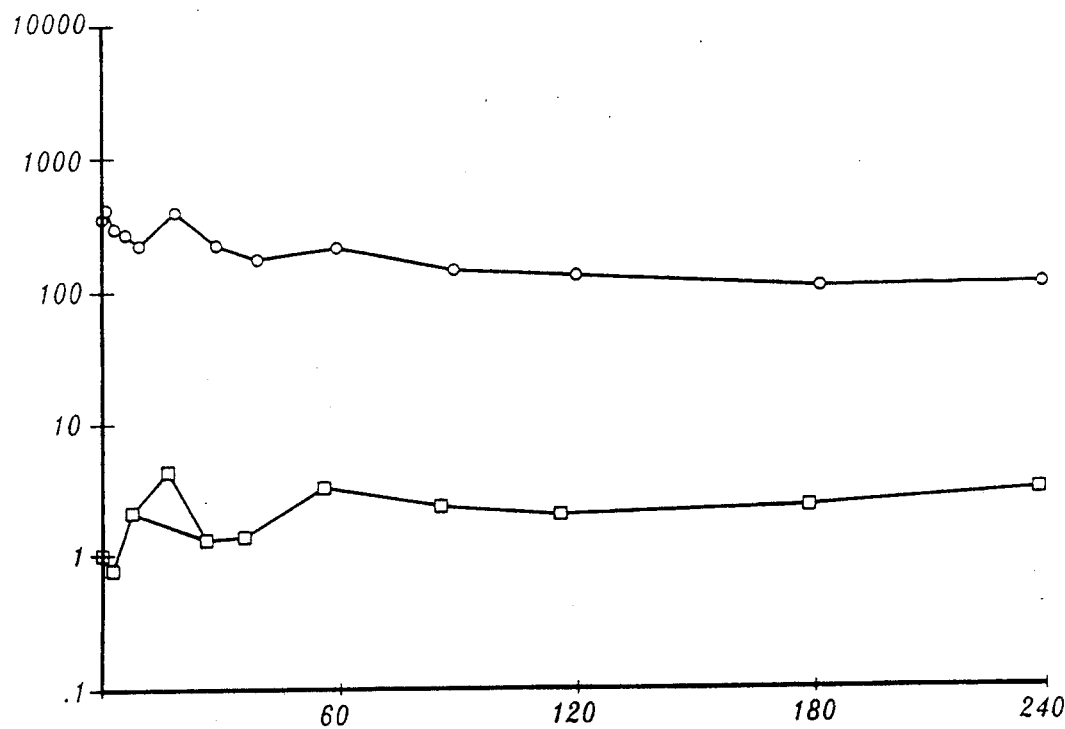

(1) MPE: % of the maximum possible effect upon the hot plate test;
(2) AUC: area under the time effect curve calculated using the MPE × Time curve. The value given indicates the dose (μg) required to produce an arbitrary AUC value of 3000; Each DE50 (μg) value (dose required to produce the maximum possible effect in 50% of the animals) presents the means of 12–18 rats. All differences between saline and CDEX groups are statistically significant by unpaired t-test at the $p < 0.05$ level.

b. Intrathecal injections in rats: effects of altering CDEX concentration on the spinal effects of opioids. Rats prepared as above received injection of morphine (3 μg/10 μl) or lofentanil (0.1 μg/10 μl) dissolved in sterile saline, concentrations which produced small but measurable analgesic effects. Other rats prepared as above received injections of these doses in concentration of CDEX of 20%, 2%, 0.2%, or 0.02%. As shown in Table 2, the optimal concentration yielding the most significant augmentation of antinociceptive (analgesic) effect in the hot plate test was 0.2% for morphine and 2% for lofentanil. Concentrations on either side of 0.2% for morphine and 2% for lofentanil yielded progressively lesser effects. FIG. 1 presents this data.

TABLE 2

Effects of varying cyclodextrin concentrations on the area under the time-effect curves of intrathecal lofentanil (0.1 μg/10 μl) or morphine (3 μg/10 μl) in rats.

| Vehicle: Intrathecal drug | Cyclodextrin concentration (% w/v) | | | | | |
|---|---|---|---|---|---|---|
| | saline | 0.002 | 0.02 | 0.2 | 2.0 | 20.0 |
| Morphine (3 μg) | 46 | 55 | 112 | 30 | 23 | 33 |
| | (0.1) | (0.5) | (0.5) | (0.9) | (0.8) | (0.5) |
| Logentanil (0.1 μg) | 0.7 | 18 | 38 | 49 | 68 | 23 |
| | (0.2) | (0.2) | (1.4) | (1.2) | (1.7) | (0.5) |

Values present the mean (SE) of the AUC/100 produced by the indicated dose of the opioid in the associated concentration of CDEX up to 20% saline.

c. Effects of CDEX on the antinociceptive effects of epidural alfentanil in dogs. Dogs were prepared with lumbar epidural catheters and chronic tracheostomies. Respiratory function curves (slope of minute ventilation (Ve) vs. endtidal $CO_2$) were measured by using the Read rebreathing technique over an endtidal $CO_2$ range of 35 to 80 mmHg $CO_2$. The skin twitch response to a thermal stimulus was used to assess the nociceptive threshold. Alfentanil (400 μg) epidurally administered in saline normally yields a short lasting (<90 min) complete block of the nociceptive endpoint (skin twitch response) and a significant respiratory depression (reduced slope of Ve vs. $CO_2$), as indicated in Table 3. The injection of alfentanil with 20% CDEX resulted in neither analgesia nor changes in respiratory function. The injection of the same dose of alfentanil in 2% CDEX results in a prolonged analgesia. FIG. 2 presents this data.

TABLE 3

Effects of epidurally administered alfentanil (400 µg) on the nociceptive threshold and the $CO_2$ response function in the dog when given in saline or 2.0, 20% 2-hydroxypropyl-$\beta$-cyclodextrin.

| | Analgensia (1) | | Respiratory function (2) |
|---|---|---|---|
| | Peak MPE | T½ | (% decrease in slope) |
| Saline | 87% | 60 min | 40 |
| 20% CDEX | 26% | 40 min | 18 |
| 2% CDEX | 100% | 180 min | 19 |

(1) Peak effect expressed as % MPE;
T½ expressed as the time (min) required for the effect to decline to approximately 50% of the maximum effect observed after the epidural injeciton of alfentanil (400 µg).
(2) values indicate the maximum percent reduction in the slope of the rate x tidal volume (Ve) response vs. $CO_2$ measured using the rebreathing techniques.

4. Localization and Redistribution a. Intrathecal injection—rats: Following the intrathecal injection of several opioids, the concentrations of the drug in spinal cord, forebrain and plasma were assessed. As indicated in Table 4, the concentrations of drug in forebrain (indicating the degree of supraspinal redistribution via the vasculature) was significantly reduced after the administration of the CDEX opiod combination in contrast to the concentrations observed when the opioids were administered in saline.

TABLE 4

Concentrations of alfentanil in brain and plasma following intrathecal injection in the rat.

| Injectate | Time of Measurement | Plasma (ng/ml) | Forebrain (mg/ml) |
|---|---|---|---|
| Morphine/saline | 5 min | 53.7 | 411. |
| Morphine/20% CDEX | 5 min | 18.1 | 140. |
| Lofentanil/saline | 5 min | 1.78 | 0.96 |
| Lofentanil/20% CDEX | 5 min | 0.41 | 0.0 |
| Alfentanil/saline | 5 min | 146. | 75.1 |
| | 45 min | 10.4 | 4.1 |
| Alfentanil/20% CDEX | 5 min | 135. | 81.6 |
| | 45 min | 10.7 | 0.0 |

Each value presents the mean of 4–5 rats.

b. Effects of CDEX on alfentanil redistribution in dogs. In dogs prepared with epidural catheters as described above, the injection of 400 µg of alfentanil in saline resulted in rapid increase to peak plasma drug concentrations. As shown in Table 5, the peak plasma concentrations and total body clearance of alfentanil measured with the coadministration of 400 µg alfentanil and 20%, and to a lesser extent 2%, CDEX were markedly reduced. The apparent volume of epidural space (Va) was increased by CDEX. Taken together, these results show that CDEX retarded the rate of redistribution of alfentanil from the epidural space to the systemic circulation.

TABLE 5

Pharmacokinetic parameters in a 3-exponential model measured in lumbar CSF after the epidural administration of alfentanil (400 µg).

| | Saline (N = 5) | 2% CDEX (N = 1) (a) | 20% CDEX (N = 1) (a) |
|---|---|---|---|
| T½abs | 1.57 | 7.2 (3.4) | 30.7 (2.2) |
| T½α | 7.9 | 7.4 (5.8) | 32.3 (7.1) |
| T½β | 116.9 | 432. (31.4) | 2179. (152) |
| C max | 1286. | 2259. (1119) | 257. (2535) |

TABLE 5-continued

Pharmacokinetic parameters in a 3-exponential model measured in lumbar CSF after the epidural administration of alfentanil (400 µg).

| | Saline (N = 5) | 2% CDEX (N = 1) (a) | 20% CDEX (N = 1) (a) |
|---|---|---|---|
| T max | 4.66 | 10.7 (71.) | —* |

T½abs: halftime of absorption (min);
T½ a: redistribution;
T½ b: elimination half life;
C max: maximum predicted concentration;
T max: time (min) to C max.
*could not be calculated for 20% CDEX.
(a): value indicates results of a single animal. Values in parenthese represents the value observed in that animal without CDEX.

5. Ex Vivo Meningeal Diffusion a. Effects of CDEX on rates of diffusion of opioids from epidural to intrathecal compartments; meningeal permeability studies (ex vivo). A diffusion cell was used to measure meningeal permeability of opioids and other drugs. Live samples of the total spinal meninges (including dura, pia and arachnoid) were dissected from freshly sacrificed Macaque nemestrina monkeys; the tissue was installed in a temperature-controlled two-well diffusion cell and kept viable by constant exposure to mechanically stirred artificial CSF (both surfaces at 37° C. continuously saturated with $O_2/CO_2$). One well (10 ml) of the diffusion cell (A) is employed for addition of 5 ml aliquots of drug in either CSF or along with various concentrations of CDEX in CSF and simultaneous with the addition of solution to well (A), an equal volume of oxygenated CSF is placed in the other well (B). Thereafter, minimal volumes (0.2–0.4 ml) of solution in well (B) are collected for assay at regular intervals for up to 2–24 hours. As volumes are withdrawn from (B), an equal volume is immediately added to maintain the original measured volume. Samples are subjected to assay by HPLC, GC-MS or radiometric methods to measure the concentrations of drug and CDEX that has diffused through the meninges. The slope of the regression line of drug concentrations in (B) vs. time is the flux from which meningeal permeability of that drug is calculated directly.

Figure 3A:
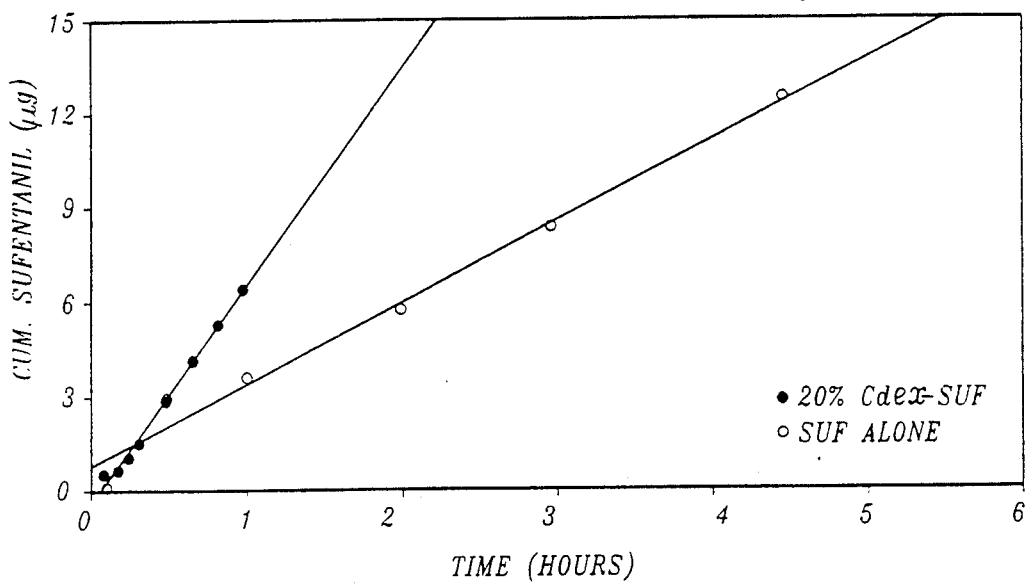
FIGS. 3A and 3B show the meningeal dural permeability of cyclodetrinincorporated sufentanil (FIG. 3A) or alfentanil (FIG. 3B) as a function of time. Each data point represents the accumulated amount (mass) of alfentanil or sufentanil that diffused through samples of total meninges (dura plus arachnoid plus pia mater from monkey spinal cord) over time. Line slopes represent meningeal flux. Solid circles are data for alfentanil or sufentanil dissolved in artificial CSF, open circles are results with alfentanil or sufentanil in 20% CDEX. The result using meninges isolated from monkey spinal cord indicates that cyclodextrin complex formation with opioids may be useful for controlling availability of analgesic drugs for meningeal transfer.
Figure 3B:
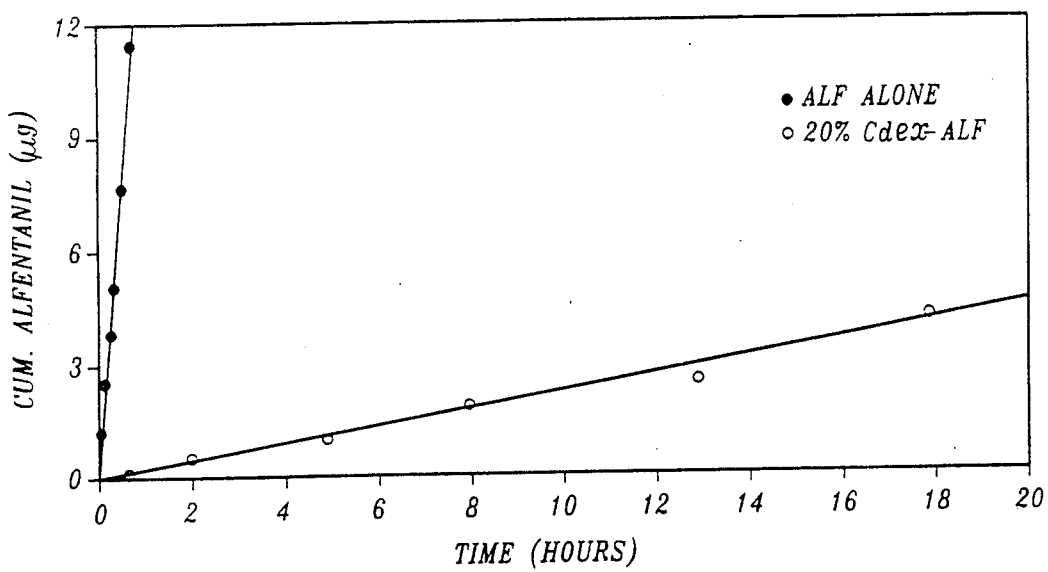

As an example of flux measurement, the movements of alfentanil and sufentanil have been examined alone (in CSF) and in CSF-CDEX at CDEX concentrations of 2% or 20%. Results show that the rate of diffusion of these agents is highly modified by the presence of CDEX. The ex vivo model also demonstrates the differential effect of CDEX on different drugs. Thus, the degree of reduction in meningeal flux, after complexation with CDEX, is alfentanil>>sufentanil (FIG. 3). In 20% CDEX, there is a 10- and 100-fold reduction for sufentanil and alfentanil, respectively. These CDEX modulations in meningeal flux of opioids shown and the relative changes in flux for the two compounds mirror those augmentations in analgesia described in the in vivo intrathecal injection model. The extent of the modulation of meningeal transfer for these model drugs through the meninges and to the spinal cord can be adjusted to reach optimal rates of epidural drug delivery to the spinal cord by employing different (optimal) concentrations (and/or molar ratios) of CDEX in combination with the drug administered. Results with the ex vivo meningeal model indicate that equivalent variations of CDEX concentrations in CDEX solutions (e.g., 20 vs. 2 vs. 0.2% CDEX, etc.) have different modulatory effects on drugs. As an example, combinations of alfentanil in 20% CDEX produce a 50- to 100-fold reduction in meningeal flux (as compared to alfentanil dissolved in CSF) while 2% CDEX reduces the rate by only 20-fold. This concentration dependency is probably a function of the molar ratio of the free drug to the unoccupied CDEX occupancy sites.

While the present invention has been described in conjunction with preferred embodiments, one of ordinary skill after reading the foregoing specification will be able to effect various changes, substitutions of equivalents, and alterations of the subject matter set forth herein. It is therefore intended that the protection granted by Letters Patent hereon be limited only by the definitions contained in the appended claims and equivalents thereof.

The embodiments of the invention in which an exclusive property or privilege is claimed are defined as follows:

1. A method of delivering an analgesic drug to the neuraxis of a patient, comprising administering said analgesic drug to the neuraxis of said patient in the form of a solution of an inclusion complex between said analgesic drug and a $\beta$-cyclodextrin substituted about 15% to about 80% with at least one substituent selected from the group consisting of $-OCH_3$, $-ROH$, $-RSO_3H$, $-CO_2R$, $-NHR$, $-NR_2$, $-NROH$, and $-SiR_3$, wherein each R is independently selected from $C_{1-10}$ alkyl groups that may be linear, branched, or cyclic, whereby said inclusion complex is effective to increase bioactivity of said drug, reduce redistribution of said drug from the neuraxis, and reduce systemic toxicity of the drug when compared to delivery of the drug alone to the neuraxis of said patient.

2. The method according to claim 1, wherein said inclusion complex is administered to said patient intraventricularly, intrathecally, or epidurally.

3. The method of claim 1, wherein said analgesic is an opioid.

4. The method of claim 3, wherein said opioid is selected from the group consisting of alfentanil, lofentanil, sufentanil, fentanyl, and morphine.

5. The method according to claim 1, wherein said drug is an antineoplastic or cancer chemotherapeutic agent.

6. The method according to claim 4, wherein said agent is methotrexate or busulfan.

7. The method of claim 1, wherein said drug is a cerebral ischemia protectant.

8. The method according to claim 1, wherein said cyclodextrin is a hydroxy ($C_{1-6}$ alkyl)-$\beta$-cyclodextrin.

9. The method according to claim 1, wherein said cyclodextrin comprises six to eight glucose molecules.

10. The method according to claim 1, wherein said complex has a molar ratio of cyclodextrin:drug of about 1:10 to about 1:10,000.

11. The according to claim 1, wherein said patient is a human.

12. The method of claim 1, wherein said inclusion complex is effective when delivered into said neuraxis of said patient to shorten the time to an ED50 maximal effect of said analgesic drug, to lower the AUC area of a time effect curve of said analgesic drug, or to lengthen the time required for said bioactivity to decline to about 50% of a maximal effect, when compared to delivery of the drug alone.

13. A composition for delivery of a drug to the neuraxis of a patient with increased bioactivity and decreased systemic toxicity, comprising a water soluble inclusion complex of an analgesic drug having a systemic toxicity, and a bioactivity when delivered into the neuraxis of a patient, complexed with a $\beta$-cyclodextrin substituted about 15% to about 80% with at least one substituent selected from the group consisting of $-OCH_3$, $-ROH$, $-RSO_3H$, $-CO_2R$, $-NHR$, $-NR_2$, $-NROH$, and $-SiR_3$, wherein each R is independently selected from $C_{1-10}$ alkyl groups that may be linear, branched, or cyclic, wherein the amount of the drug and the substituted $\beta$-cyclodextrin in the inclusion complex are effective to increase said bioactivity of said drug, reduce redistribution from the neuraxis, or to reduce said systemic toxicity when delivered into the neuraxis of said patient, as compared to delivery of the drug alone to the neuraxis of the patient.

14. The composition of claim 13, wherein said analgesic is an opioid.

15. The composition according to claim 14, wherein said opioid is selected from the group consisting of alfentanil, lofentanil, sufentanil, fentanyl, and morphine.

16. The composition according to claim 13, wherein said drug is an antineoplastic agent.

17. The method according to claim 16, wherein said agent is methotrexate or busulfan.

18. The method according to claim 13, wherein said drug is a cerebral ischemia protectant.

19. The composition according to claim 13, wherein said cyclodextrin is a hydroxy ($C_{1-6}$ alkyl)-$\beta$-cyclodextrin.

20. The composition according to claim 13, wherein said cyclodextrin comprises six to eight glucose molecules.

21. The composition according to claim 13, wherein said complex has a molar ratio of cyclodextrin:drug of about 1:10 to about 1:10,000.

* * * * *

UNITED STATES PATENT AND TRADEMARK OFFICE
CERTIFICATE OF CORRECTION

PATENT NO. : 5,180,716

DATED : January 19, 1993

INVENTOR(S) : T.L. Yaksh et al.

It is certified that error appears in the above-identified patent and that said Letters Patent is hereby corrected as shown below:

| COLUMN | LINE | |
|---|---|---|
| 1 | 60&61 | "in-trasisternal" should read --intracisternal-- |
| 2 | 54 | "prostagladin" should read --prostaglandin-- |
| 3 | 46 | "cyclodetrinincorporated" should read --cyclodetrin-incorporated-- |
| 10 | 51 | "ay" should read --any-- |
| 11 | 12 | delete "of" (third occurrence) |
| 12 (Table 2) | 47 | "inthe" should read --in the-- |
| 13 (Table 3) | 5 | "Analgensia" should read --Analgesia-- |
| 13 | 25 | "opiod" should read --opioid-- |
| 13 (Table 5) | 67 | "432" should read --324-- |
| 14 (Table 5) | 13 | "parenthese" should read --parentheses-- |

Signed and Sealed this

Seventh Day of December, 1993

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO. : 5,180,716
DATED : January 19, 1993
INVENTOR(S) : T.L. Yaksh et al.

It is certified that error appears in the above-identified patent and that said Letters Patent is hereby corrected as shown below:

Column 1, line 4, before "Technical Field," insert:

--This invention was made with Government support under Grant DA05513 and Grant CA38552, awarded by the National Institute of Health. The Government has rights in this invention.--

Signed and Sealed this

Third Day of January, 1995

Attest:

BRUCE LEHMAN

Attesting Officer    Commissioner of Patents and Trademarks